Figures 1, 2:
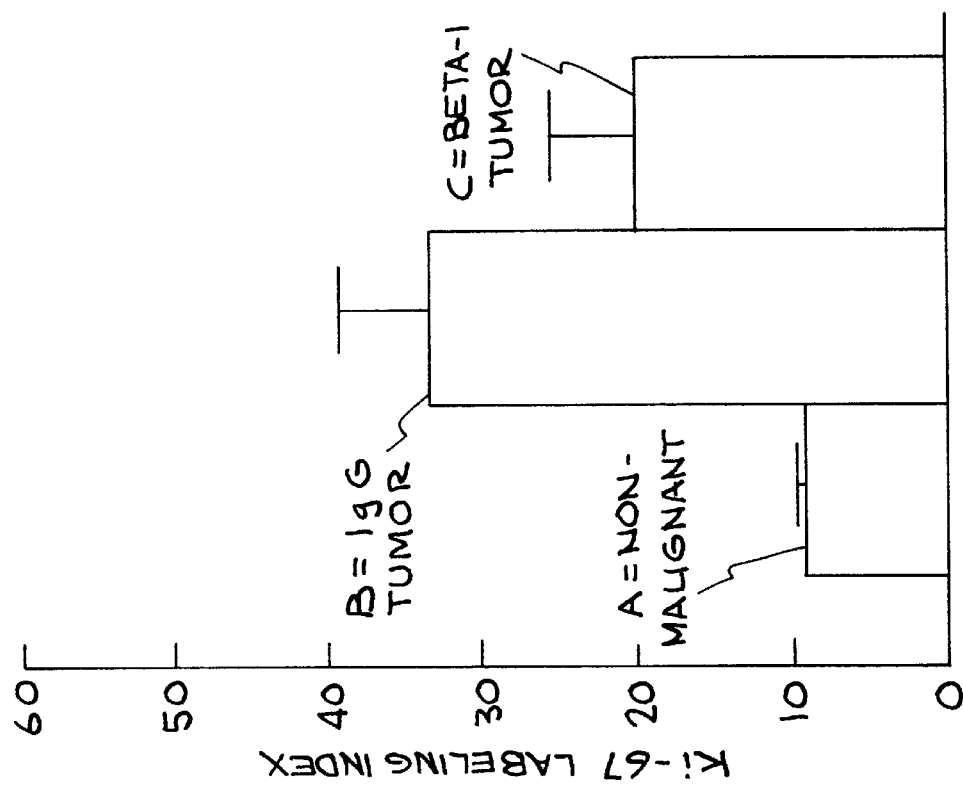

United States Patent [19]

Bissell et al.

[11] Patent Number: 5,846,536
[45] Date of Patent: Dec. 8, 1998

[54] RESTORATION OF NORMAL PHENOTYPE IN CANCER CELLS

[75] Inventors: Mina J. Bissell, Berkeley; Valerie M. Weaver, Oakland, both of Calif.

[73] Assignee: The Regents of the University of California, Oakland, Calif.

[21] Appl. No.: 726,230

[22] Filed: Oct. 4, 1996

[51] Int. Cl.$^6$ .................. A61K 39/395; C07K 16/00; C12P 21/08

[52] U.S. Cl. ................. 424/158.1; 424/130.1; 424/132.1; 424/141.1; 424/143.1; 424/144.1; 424/152.1; 424/172.1; 530/387.1; 530/388.22; 530/388.23; 530/388.24; 530/388.85; 530/389.2

[58] Field of Search ............. 424/130.1, 132.1, 424/141.1, 143.1, 152.1, 172.1, 144.1, 158.1; 530/387.1, 388.22, 388.23, 388.24, 388.85, 389.2

[56] References Cited

PUBLICATIONS

Inhibition of Cell Attachment, Invasion and Mestasis of Human Carcinoma Cells by Anti–integrin B1 Subunit Antibody. Jpn. J. Cancer Research 83, pp. 1317, 1320, 1325, Dec. 1992.
Koretz et al. (1994) Virchows Archiv 425:229–236.
Fujita et al. (1992) Jpn. J. Cancer Res. 83:1317–26.
Amar et al. (1994) J. Neuro–Oncol. 20:1–15.
Pignatelli et al (1992) Br. J. Cancer 66:629–34.
Streuli et al (1991) J. Cell Biol. 115:1383–95.
Dermer, G.B. (1994) Biotechnol. vol. 12: p. 320.

*Primary Examiner*—Lila Feisee
*Assistant Examiner*—Geetha P. Bansal
*Attorney, Agent, or Firm*—Paul R. Martin; Pepi Ross

[57] ABSTRACT

A method for reversing expression of malignant phenotype in cancer cells is described. The method comprises applying $\beta_1$ integrin function-blocking antibody to the cells. The method can be used to assess the progress of cancer therapy. Human breast epithelial cells were shown to be particularly responsive.

8 Claims, 6 Drawing Sheets

RESTORATION OF NORMAL PHENOTYPE IN CANCER CELLS

This invention was made with U.S. Government support under Contract No. DE-AC03-76SF00098 between the U.S. Department of Energy and the University of California for the operation of Lawrence Berkeley Laboratory. The U.S. Government may have certain rights in this invention.

I. BACKGROUND OF THE INVENTION

1. Field of the Invention

This invention relates generally to control of the mechanism by which epithelial cells become malignant and more specifically to treatment and diagnosis of carcinoma.

2. Description of Related Art

The development and phenotypic expression of overt cellular malignancy has long been associated with changes in the cells' genome. In January 1982 (Bissell, M. J., Hall, H. G., and Parry, G.; "How Does the Extracellular Matrix Direct Gene Expression?", *J. Theor. Biol*, 99: 31–68, 1982) Bissell et al. reported an epithelial cell model wherein the extracellular matrix (ECM) affected chromatin structure and thereby gene expression through its connection to the nuclear matrix and cytoskeleton. A cell's ability to synthesize competent ECM was in turn predicted to be a function of the chemical and mechanical properties of the culture milieu. Thus a dynamic reciprocity between the genome and the ECM was postulated.

Petersen, Bissell, and others (Petersen et al., Proc. Natl. Acad. Sci. USA, 89:9064–9068, 1992) developed an assay system to distinguish the growth and differentiation pattern of normal and malignant human breast epithelial cells. Using a reconstituted basement membrane (BM) they were able to culture normal human breast epithelial cells and corresponding carcinoma cells. They demonstrated, for the first time, that normal cells re-expressed their in-vivo differentiated morphology in culture. Single cells formed multicellular spherical colonies with a final size similar to true acini in situ. These normal colonies exhibited many other attributes, normally seen only in situ: a central lumen surrounded by polarized luminal epithelial cells, three dimensional cellular architecture, biochemical expression consistent with mammary epithelial cell biology, and growth inhibition. In contrast, the carcinoma cells and cells from biopsy specimens had growth rates that were unaffected in the reconstituted basement membrane and they continued to express the undifferentiated phenotype typical of the tumor state.

Streuli and Bissell reported in (J. Cell Biol, 115:1383–1395, 1991) that in mouse mammary epithelial cells (MEC) the $\beta_1$ integrin receptor played a key role in transmitting signals necessary for growth, differentiation, and survival, between the extracellular matrix and the cell interior. Observations by Boudreau et al. (Science, 267:891–893 Feb. 10, 1995) strengthened that observation and Howlett et al. (Howlett, A. R., Bailey, N., Damsky, C., Petersen, O. W., and Bissell, M. J.; "Cellular Growth and Survival are Mediated by Beta-1 Integrins in Normal Human Breast Epithelium But Not in Breast Carcinoma, "J. Cell Sci., 108: 1945–1957, 1995) extended those observations to include a phenotypically normal cell line of human MEC. Normal mouse MECs cultured in a reconstituted basement membrane were protected from apoptosis. If the ability of the normal cells' $\beta_1$ integrin receptor to interact with the basement membrane was blocked with a specific antibody, the cells died. These results supported the notion that $\beta_1$ integrin receptors are important for competent interaction between the ECM and the cell and are necessary to maintain the normal differentiated state of MECs.

In the Japanese Journal of Cancer Research, 83:1317–1326, December 1992, Fujita et al. reported that a newly established anti-human $\beta_1$ subunit monoclonal antibody inhibited the invasion and metastasis of human bladder carcinoma cell and human gastric carcinoma cells in nude mice. They postulated that $\beta_1$ integrins play an important role in tissue attachment, migration, invasion and metastasis of human carcinoma cells.

II. SUMMARY OF THE INVENTION

The extracellular matrix (ECM) of mouse breast epithelial cells, through the $\beta_1$ integrin receptor molecule and its heterodimer family, transduces chemical and structural information from the exterior to the interior of the cell and influences gene expression, including functional differentiation (Streuli, C. et al, J. Cell Biol. 115:1383–1395, 1991). Malignant and non-malignant human breast epithelial cells can be distinguished from one another in culture when the culture environment comprises reconstituted basement membrane (Petersen et al., Proc. Natl. Acad. Sci. USA, 89:9064–9068, 1992). Normal epithelial cells, when cultured in reconstituted basement membrane, synthesize and deposit on organized endogenous basement membrane. Chemical and structural signals exchanged between the ECM and cell are critical to maintaining normal cell function. Furthermore, if the interaction between the ECM and the cell is obstructed, the normal cells apoptose. Tumor cells do not die under the same conditions. Malignant cells, similarly cultured in a reconstituted basement membrane, fail to synthesize an ECM that is competent to support the exchange of information between the ECM and cell. The normal cell phenotype expression is maintained only when a dynamic reciprocity exists between the ECM and the cell.

It is an object of the invention to take advantage of any role the ECM plays in expression of malignancy in human breast epithelial cells. It is a further object of the invention to manipulate the ECM or extracellular micro-environment to reverse malignant behavior in tumor cells. It is an additional object of the invention to quickly assess in culture whether a treatment to reverse malignant expression is successful and to be able to correlate phenotypic expression in culture with phenotypic expression in situ.

The present invention provides a method for reversing the expression of the malignant phenotype in epithelial cells. The method is preferably applied to reproductive cells, such as breast and prostate cells, however any epithelial cell type that, in its normal state, responds to a basement membrane that comprises more than about 20% to 30% of the combination of laminin and collagen type IV by synthesizing ECM, is a target for the inventive method. One such example would be intestinal brush border epithelial cells. Generally, any epithelial cell that, in its normal state, has $\beta_1$ integrin trans-membrane receptors is a target for the inventive method. More specifically, any epithelial cell that, in its normal state, has $\alpha_x\beta_1$, such as $\alpha_3$ $\beta_1$ or $\alpha_6\beta_1$ trans-membrane receptors is a target for the inventive method. The method comprises applying $\beta_1$ integrin function-blocking antibody to the cells. However other integrin-specific function-blocking antibodies, or synthetic inhibitory peptide sequences, directed against either $\beta_1$ integrin receptors or specific heterodimer receptors such as $\alpha_6\beta_1$ or $\alpha_3\beta_1$ or other heterodimer integrin molecules are predicted to have the same effect. Human breast epithelial cells were shown to be particularly responsive. The invention can be used as a cancer therapy to prevent the invasion and spread of cancer cells, further malignant transformation, and to limit growth of metastasis. Further, an assay system for the expression of normal and malignant phenotype of human breast epithelial cells is provided. Additionally, a cell culture assay that corresponds to normal and malignant breast tissue in situ is provided.

III. SUMMARY DESCRIPTION OF THE DRAWINGS

FIG. 1: shows the effect of restoration treatment on the thymidine labeling index.

FIG. 2: shows the effect of restoration treatment on the Ki-67 labeling index.

Figures 3, 4:
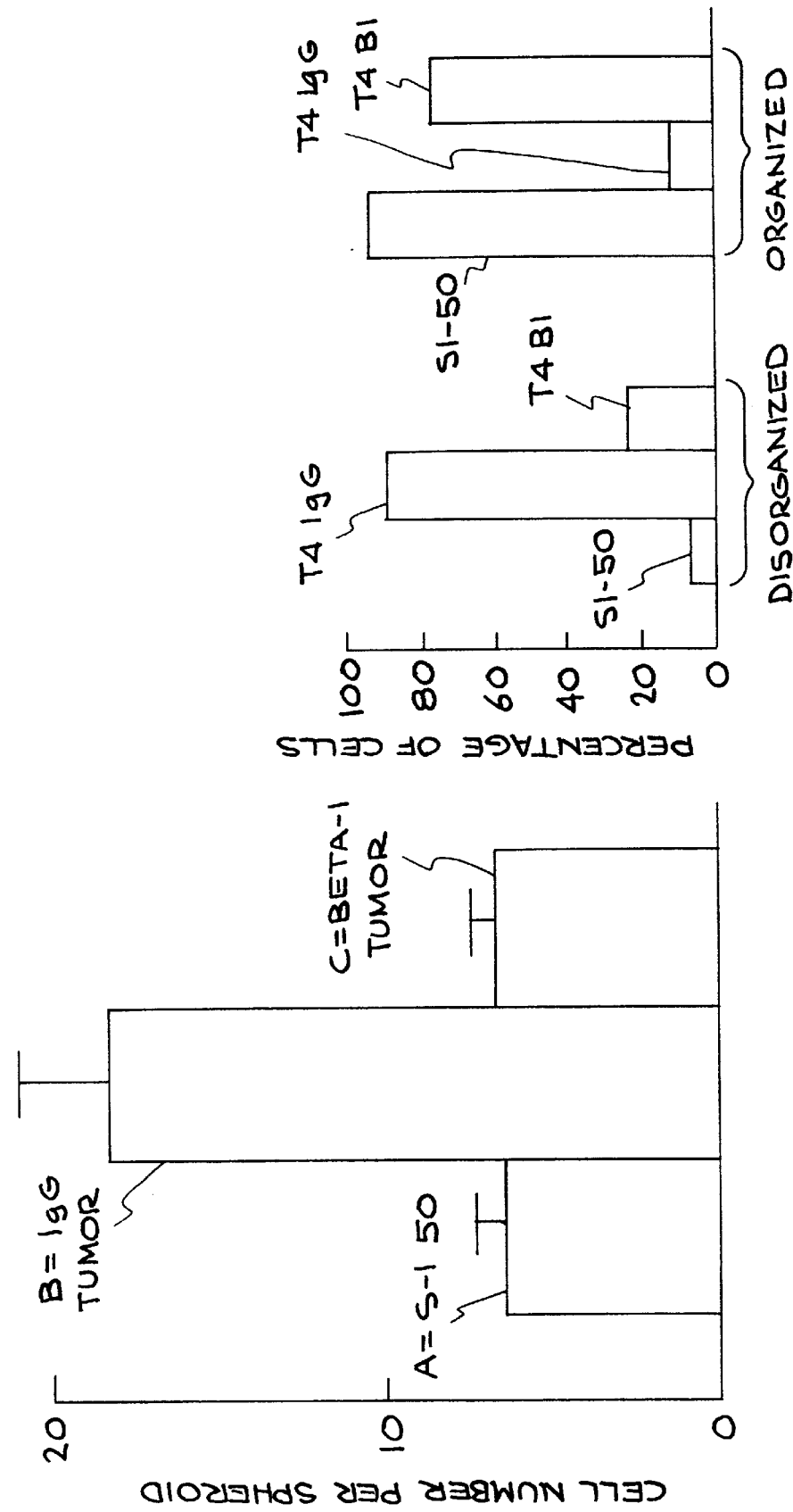

FIG. 3: shows the effect of restoration treatment on the number of cells per spheroid colony.

FIG. 4: shows the effect of restoration treatment on colony organization.

FIG. 5A: shows phalloidin staining of filamentous actin in frozen sections of 3D cultures of non-malignant S-1 50 cells.

Figure 6A:
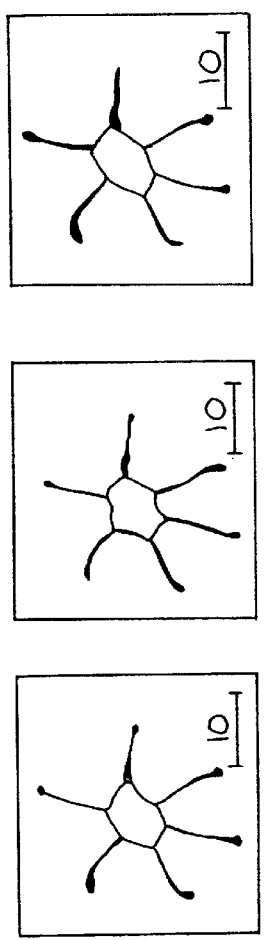

FIG. 6A: shows ability of cells to form adherens junctions by immunostaining sections of 3D cultures of non-malignant S-1 50 cells with anti-human E cadherin antibodies and Texas-red secondary antibody, on days 10, 11, and 12 of culture.

Figure 6B:
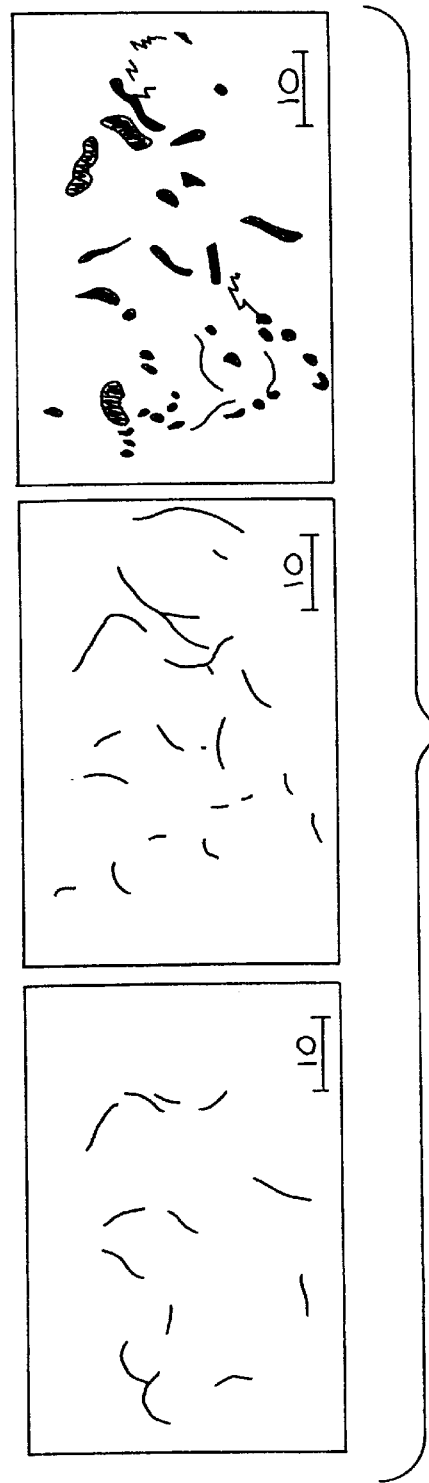

FIG. 6B: shows ability of cells to form adherens junctions by immunostaining sections of 3D cultures of T-4 tumor cells after treatment with control antibody, on days 10, 11 and 12 of culture.

Figure 6C:
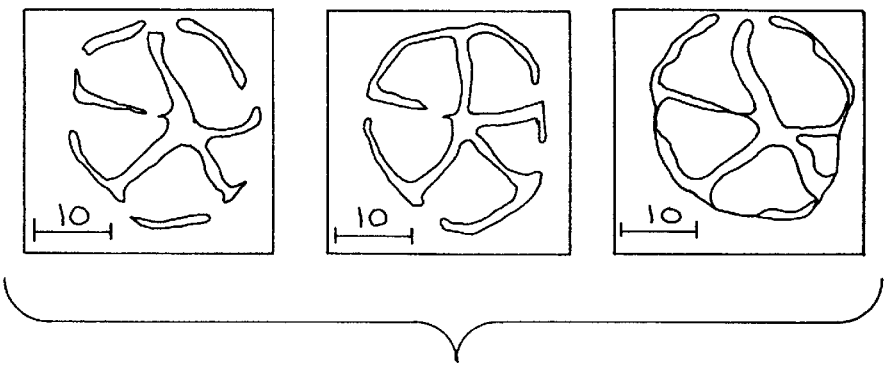

FIG. 6C: shows ability of cells to form adherens junctions by immunostaining sections of 3D cultures of T-4 tumor cells after treatment with $\beta_1$ integrin function-blocking antibody, on days 10, 11 and 12 of culture.

Figure 7:
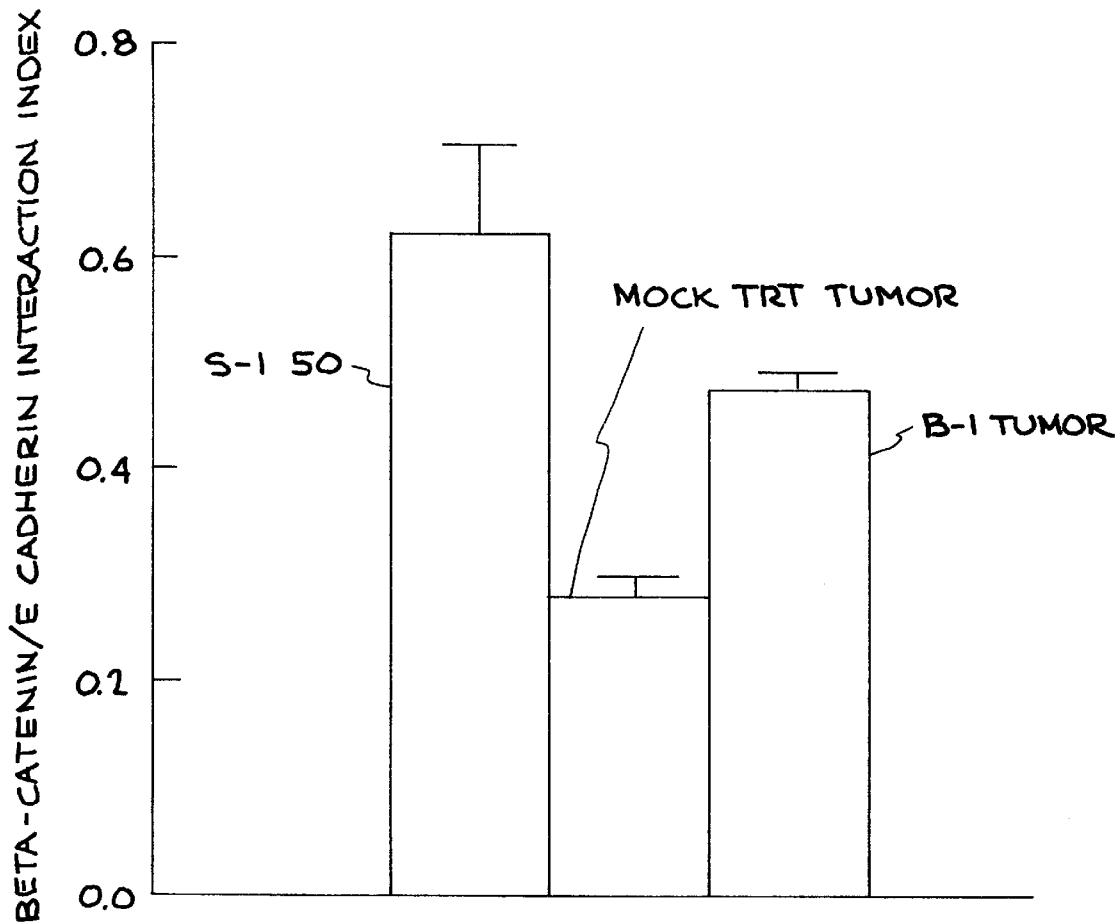
Figures 8A, 8B:
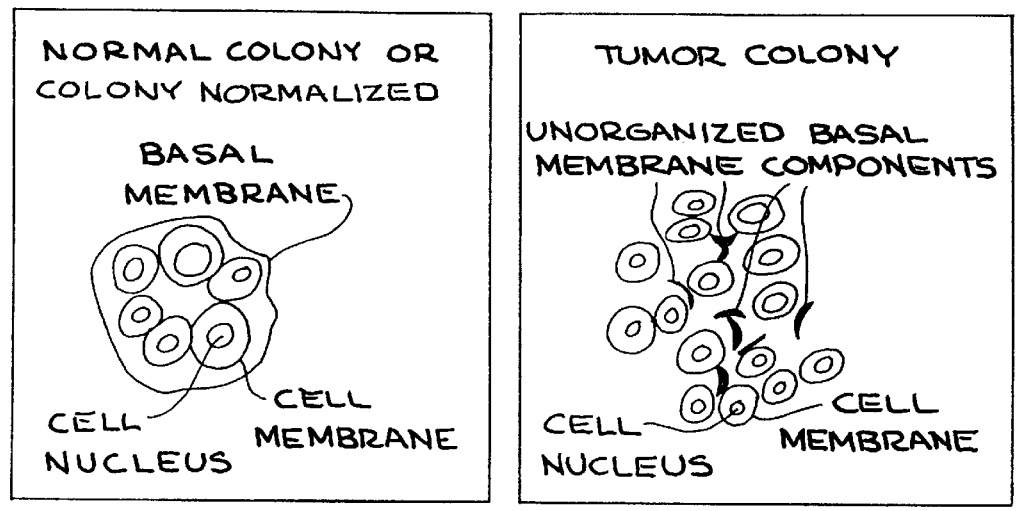

FIG. 7: shows the effect of restoration treatment on β-catenin/E cadherin interactions. FIG. 8A: shows untreated S-1 50 non-malignant cells or T-4 tumor cells treated with $\beta_1$ integrin function-blocking antibody, immunostained for the presence of basally deposited collagen IV.

FIG. 8B: shows T-4 tumor cells treated with control antibody, immunostained for the presence of basally deposited collagen IV.

Figure 9:
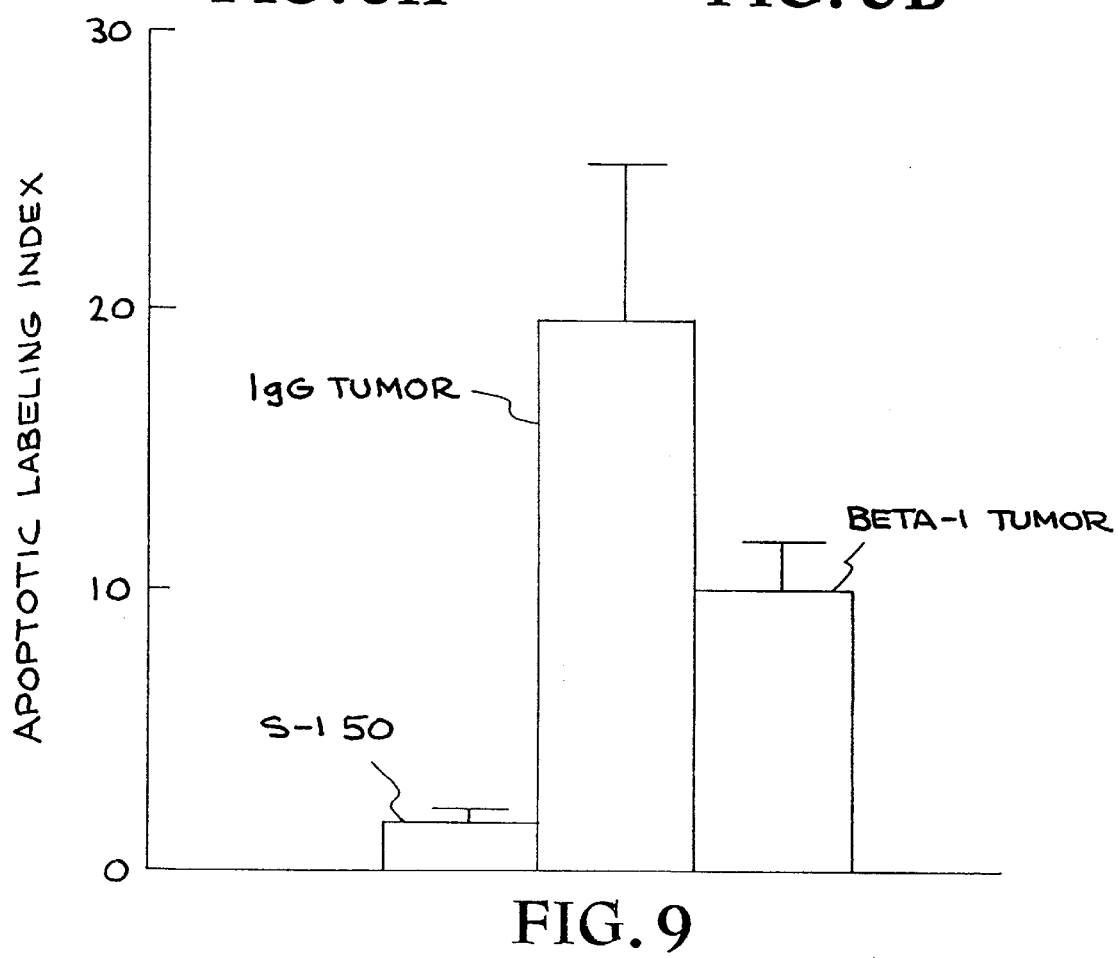

FIG. 9: shows the effect of restoration treatment on basal apoptosis rates.

IV. DETAILED DESCRIPTION OF THE INVENTION

The present invention provides a method for reversing expression of malignancy in cells comprising applying $\beta_1$ integrin function-blocking antibody to the exterior of the cells. Certain molecules, such as antibodies, when applied to a tumor cell restore or augment the ECM's ability to interact with the cell in a way that is important for re-expression of a nonmalignant phenotype, dominating the malignant cellular genotype. More specifically, application of $\beta_1$ integrin antibody to a malignant breast epithelial cell reverses expression of the malignant phenotype. Other anti-integrin inhibitory antibodies or peptide inhibitors have the same effect in other types of cancer, depending upon the initial integrin profile expressed by the cell.

By use of the term "normal cell" herein is meant a biological cell that doesn't express a malignant phenotype.

By use of the term "normal cell colony" herein is meant a cell colony made up of cells that don't express a malignant phenotype.

By use of the term "three dimensional (3D) culture matrix" herein is meant a cell culture substrate comprising elements necessary for a normal cell to form a competent extracellular matrix when in culture.

By use of the term "$\beta_1$ trans-membrane receptor" or "$\alpha_x\beta_1$ trans-membrane receptor" herein is meant a protein that is an integral part of plasma membrane and has a extracellular matrix ligand binding site on the extracellular domain.

By use of the term "$\beta_1$ integrin function-blocking antibody" herein is meant a monoclonal anti-human $\beta_1$ integrin antibody whose interaction with the $\beta_1$ integrin receptor on the plasma membrane of the cell inhibits the interaction with its ECM substrate or alters the downstream signaling of the $\beta_1$ integrin receptor.

By use of the term "candidate antibody" herein is meant an antibody or portion thereof, that when applied to a group of cells expressing malignant phenotype, may cause the reorganization of the group of cells into a colony formation wherein the cell organization is characteristic of non-malignant cells.

By use of the term "TUNEL staining" herein is meant terminal transferase mediated FITC dUTP labeling of endonuclease induced DNA strand breaks associated with the process of apoptosis.

There are several parameters that are different in tumor cells and normal cells and can be used to determine quantitatively whether a cell will grow malignantly or nonmalignantly in situ. Using a three dimensional (3D) culture assay system (A. R. Howlett, N. Bailey, C. Damsky, O. W. Petersen, & M. J. Bissell, *Cellular growth and survival are mediated by $\beta_1$ integrins in normal human breast epithelium but not in breast carcinoma*, J. Cell Sci. 108:1945–1957, February 1995, incorporated herein by reference) the present invention has been shown to reverse malignancy and restore expression of a nonmalignant phenotype to tumor cells in culture. Further, expression of cell malignancy or nonmalignancy in this 3D culture system provides an accurate assay of the cells' expression in situ.

Malignant behavior and the restoration of non-malignant behavior by the treatment, was determined using four separate criteria and their associated methodologies. The behavior of the cells was analyzed in three dimensional basement membrane cultures before and after treatment and compared to the behavior of a non-malignant mammary epithelial cell line by: examining effects on cell proliferation, cell and colony morphology and by determining the cell' ability to respond appropriately to a basement membrane by assessing dynamic reciprocity criteria. The behavior of the cells in vivo was also analyzed by injecting tumor and treated tumor cells subcutaneously into nude mice and scoring for the formation of and size of tumors.

Colony morphology measurements yielded the most rapid response. After application of $\beta_1$ integrin function-blocking antibodies to malignant human breast epithelial cells, colony growth patterns characteristic of a nonmalignant phenotype were observed within 3 to 4 days.

A unique human breast cancer cell model, HMT-3522, developed by Dr. O. W. Petersen was used to test and evaluate the invention. This progressive cell series exhibits a range of states in progression from normal to malignant phenotype. Many of the cell passages behave like normal cells when cultured with a reconstituted, exogenous, basement membrane. The series was established by culturing and passaging the primary cells for several passages, after which a spontaneously immortalized cell line grew. This cell line was dependent on EGF and was denoted S-1. Each passage was noted by adding the passage number to the S-1 notation. For example cells from the 50th passage are denoted, "S-1 50". The primary and S-1 cells were always grown in the presence of epidermal growth factor (EGF) under serum-free conditions. An EGF-independent cell line, denoted S-2, was established from an S-1 118 clone by growth in an EGF-free, serum-free medium. It was designated "S-2 119". At approximately passage 238, after subcutaneous injection into nude mice, some S-2 cells spontaneously transformed to become malignant. One of these was cloned, passaged, and reinjected into nude mice. Cells from this tumor were isolated to establish the tumorgenic cell passage, denoted T-4.

Data show that continued passage and selection of these cells in chemically defined media, for more than 300 passages, resulted in spontaneous malignant transformation. Thus while early passage cells behave like reduction mammoplasty epithelial cells, late passage cells behave like primary tumor cells. Cells along the passage continuum demonstrate a progressive transformation phenotype. Interestingly, cells throughout the continuum spontaneously sustain many of the frequently detected gene alterations observed in aggressive, recurrent human breast cancer biopsies. Thus passages S1 40–60 reproducibly exhibit a p53 mutation; passage S-1 100–130 demonstrates a cmyc amplification; and S-2 and T4 EGF-independent cell passages exhibit EGF receptor and cerb-B2 amplifications. Using our novel 3 D BM assay, we observed that these passages also sustain refractoriness to cues from the extracellular matrix. For example, primary cultures and established cell lines of tumorgenic breast cells grown in exogenous 3 D basement membrane, form large disorganized spheroids and fail to growth arrest or deposit basement membranes. In contrast, nontumorgenic breast cells grown in identical conditions deposit an organized, functional, endogenous basement membrane, growth arrest, and undergo mammary epithelial cell morphogenesis. Our data demonstrate that early passage S-1 50 HMT-3522 cells behave similar to nontumorgenic mammary cells while late passage T4 HMT-3522 tumorgenic cells behave identical to primary tumor cells. Surprisingly, pre-malignant passage S-2 220 HMT-3522 cells demonstrate a unique phenotype. Thus, similar to malignant HMT cells they fail to deposit an organized, functional, endogenous basement membrane even when cultured in an exogenous basement membrane. A subset of these cells do however form extremely large disorganized, spheroids, 2–3 times the size as those formed by the tumor cells, strongly indicating a defect in the apoptotic pathway exists in these cell passages.

Table 1 summarizes the response of cells to tests for the malignant phenotype. The cells were examined after a varying number of passages in culture. The cells in early passages are essentially nonmalignant whereas the T4 cells are essentially

TABLE 1

| MALIGNANT PHENOTYPE | PASSAGE #: | | | | |
|---|---|---|---|---|---|
| PARAMETER | S-1 50 | S-1 105 | S-1 175 | S-2 | T4 |
| Loss of ability to growth arrest | | | | XX½ | XXX |
| Loss of ability to organize cells in a colony | | X | XXX | XXX | |
| Loss of ability to organize | | | | XXX | XXX |

TABLE 1-continued

| MALIGNANT PHENOTYPE | PASSAGE #: | | | | |
|---|---|---|---|---|---|
| PARAMETER | S-1 50 | S-1 105 | S-1 175 | S-2 | T4 |
| endogenous basement membr. | | | | | |
| Loss of ability to control apoptosis | | X | XX | XX½ | XXX |
| Percent cells | 5% | 12% | 15% | 18% | 30% |
| Normal phenotype expressed upon application of $\beta_1$ Ab | | | | unknown | XXX |
| Cell death if $\beta_1$ integrin is blocked by $\beta_1$ antibody | XXX | XX½ | XX | X | |
| Percent cells | 70–80% | 50–60% | 30% | 15% | 10% |

Note that T4 cells revert to normal phenotype when $\beta_1$ integrin function-blocking antibody (Ab) is applied but that normal cells die as a result of application of the $\beta_1$ integrin function-blocking antibody. The level of response, of course, varies as a function of the concentration of applied Ab. It is important to use the correct concentration of $\beta_1$ function-blocking Ab to balance these two effects. In some cases the $\beta_1$ Ab may be best used as an adjunct therapy to other treatments.

Examples

Cells were grown in an exogenous basement membrane culture according to the procedures below and described in part in Proc. Natl. Acad. Sci. USA, 89:9064–9068 and in J. Cell Sci. 108:1945–1957, February 1995.
Briefly, the following materials and solutions were assembled:

1. Frozen basement membrane made from Englebreth-Holm-Swarm (EHS) tumors, made in house according to procedures described in R. W. Orkin et al. J. Exp Med, 145:204–220, 1975, or Matrigel Matrix commercially available from Collaborative research or Becton Dickinson, or other similar three dimensional (3D) culture matrix;
2. Soybean Trypsin Inhibitor-available from Sigma type I-s T6522 10 mg/ml stock;
3. Fresh serum-free DMEM/F12 media with additives, including hydrocortisone, insulin, transferrin, prolactin, estrogen and sodium selenite;
4. Multiwell plates (plastic tissue culture grade);
5. sterile Eppendorf tubes; and
6. Cells to be assayed, grown on plastic or vitrogen to near confluence in serum free medium Then the 3-D EHS assay procedure comprising the following steps was followed:

1. Approximately 24 hours prior to the assay thaw a vial of EHS or Matrigel out in a thermos on ice in the refrigerator (EHS or Matrigel gel and cannot be allowed to increase in temperature above 4° C.). Adjust the EHS or Matrigel protein concentration between about 10 mg/ml and about mg/ml (as determined by a conventional Bradford protein assay) using serum-free medium plus appropriate additives.
2. One hour prior to putting the cells into EHS or Matrigel, plate a small amount of EHS or Matrigel on the bottom of the multiwell plates-100μl should suffice-use a microtip to spread the basement membrane evenly across the plastic surface.

3. Place coated plates in a 37° C. incubator to allow the coating to harden.
4. Trypsinize the cells to be plated-the cells will need to be trypsinized sufficiently to obtain good single cell suspensions-otherwise even EHS or Matrigel suspensions will not be obtained. Wash the cells in serum-free-additive free medium at least once.
5. Add 75–100 μl of soybean trypsin inhibitor per 10 ml of cell suspension during the washing procedure to inactivate the trypsin.
6. Count the cells and do trypan blue viability to ensure that there is a very low proportion of nonviable cells-less than 5% is acceptable.
7. Adjust cell counts to $1.0 \times 10^6$ cells/per ml of serum free medium.
8. Pipet 250 μl of cell suspension into each Eppendorf tube-which will be sufficient for a good 300 μl 3 dimensional cell culture-final concentration set at 250,000 cells per 300 μl culture.
9. Spin the cell suspensions in the Eppendorf tubes in a microfuge for 4–5 minutes on a low speed-i.e. setting 4 should be sufficient to get a pellet without damaging the cells.
10. Aspirate off the supernatant and place the tubes with the cells on ice for a few minutes to chill.
11. Using a 1000 μl pipette tip and an Eppendorf pipettor carefully remove 300 μl of EHS or Matrigel from the stock solution. You will need to work fairly quickly here. Make sure that you do not pipette up too fast as the matrix is quite viscous and you also do not want to introduce air bubbles. We usually hold the end of the pipette with a bit of tension to prevent air from being drawn up into the tip.
12. Carefully pipette about 50 μl of this matrix into one of the Eppendorf tubes gently disrupting the pellet of cells to get the cells into a concentrated suspension If you do not do this you will end up with a compacted pellet of cells which will be near impossible to resuspend-then carefully pipette the rest of the matrix into the Eppendorf tube gently up and down to obtain a uniform cell suspension without introducing air bubbles. This is best achieved by keeping tension on the pipettor at all times and not pipetting the full contents of the matrix into the Eppendorf tube.
13. Carefully pull almost all of the matrix/cell suspension into the pipette tip-don't be greedy-leave some cells in the bottom if you have to-this avoids air bubbles. Then gently expel the tip contents into the multiwell plates precoated with matrix. Steps 11–13 need to be done fairly quickly as the gel will begin to harden if you take too long and you will end up with an uneven culture suspension. After you are finished place the cultures in a 37° C. incubator for 1 hour to allow the cultures to harden.
14. Once the matrix has hardened add 700–1000 μl of serum free medium with appropriate additives and place the cultures back into the incubator.
15. The cultures need to have the media changed at least every 2nd day. We do not use antibiotics in our cultures therefore care must be taken to ensure that good aseptic technique is followed at all times. The matrix gel is fairly sturdy but care should be exercised to avoid aspirating up bits of the gel when media changing-therefore turn the suction down-and gently pipette your media changes holding your cultures at an angle.
16. Single cells will begin to grow after 1 day (can be assessed by BrDu or thymidine labeling) and nontumorigenic cells will begin to undergo morphogenesis by day 3–4 or 5–6 depending upon the cells tested. Cell growth arrest and mature spheroids can be expected by days 7–8 when cells typically enter $G_0$.

The Matrigel, preferably contains between about 10% and 99% laminin. More preferably it contains between about 20% and 90% laminin; most preferably it contains between 50% and 80% laminin.

Basement membrane (BM) is a specific 3D culture matrix made of about 80% laminin, about 10% type IV collagen, about 10% proteoglycans (including various glyoproteins such as entactin, and fibronectin), and, optionally, growth factor.

Medium is prepared as described in Petersen et al., Proc. Natl. Acad. Sci. USA, 89:9064–9068, 1992 and by R. Blaschke et al. Cell Differentiation by Extrracellular Matrix Components, Methods in Enzymology, 245:535, 1994. The medium used by the inventors was designated H14 and comprised DMEM/F12 having 15 millimolar (mM) HEPES buffer with L-glutamine and without sodium bicarbonate, purchased from Life Technologies (cat. no. 12400–024); the reagents listed below were also added to the medium. The DMEM and other biological reagents are available from many other commercial sources such as Gibco or BRL.

The following reagents were added to the media formulation:

| | | |
|---|---|---|
| Insulin | 250 ng/ml | Boehringer Mannheim |
| Prolactin | 5 μg/ml | Sigma Biochemical |
| Transferrin | 10 μg/ml | Sigma Biochemical |
| Sodium Selenite | 2.6 ng/ml | Collaborative Research |
| Estradiol | $10^{-10}$ Molar (M) | Sigma Biochemical |
| Hydrocortisone | $1.4 \times 10^{-6}$ M | Collaborative Research |
| Epidermal Growth Factor | 10 ng/ml | Collaborative Research |

Of the above additives, insulin, transferrin, and sodium selenite are necessary for proper cell growth. Prolactin, Estradiol, and hydrocortisone are preferable but most cells will grow in their absence. Epidermal Growth Factor (EGF) is necessary for growth-factor dependent non malignant cells, but is not necessary for cells expressing growth-factor independent malignant phenotype.

The specific reagents used are listed in amounts that worked well with the cell system, however, many changes can be made in the formulation without adversely affecting the results. It is well known to practitioners in the art of cell culture, how to adjust these components without significantly affecting the cell response. The important point is that the cells must be grown in a 3D culture matrix.

To treat cells with antibody, a preparation of AIIB2 monoclonal anti-human $\beta_1$ integrin function-blocking antibody ascites protein concentration was adjusted to between about 30 and about 35 mg/ml using sterile serum-free medium. This corresponds roughly to between about 3 and about 3.5 mg/ml $IgG_1$ active antibody, as estimated from a coomassie stained gel. A dilution of between about 1:100 and about 1:200 was used in the reconstituted basement membrane, corresponding approximately to between about 300–350 μg/ml and about 150–175 μg/ml active antibody, resulting in about 95% complete restoration of all tumor colonies to non-malignant behavior. The tumor cell seeding rate was approximately $1 \times 10^6$ cells per ml of reconstituted basement membrane. The antibody treatment strategy comprised mixing the selected antibody with the reconstituted basement membrane and proceeding with the culturing as per our normal protocol. Visual effects were observed as early as 3 days after seeding.

As described above, cells can be treated with antibodies that bind to the functional integrin site. As an alternative, antibody fragments that bind to the functional integrin site, or peptides that bind to the functional integrin site can be substituted for antibodies in the above treatment method.

For control experiments, nonspecific rat IgGs were obtained from Jackson Immunologicals. The anti $\beta_1$ integrin-function blocking antibodies, AIIB2, (which were obtained from rat monoclonals) were provided by C. Damsky, (Professor in Research, Department of Stomotology, University of California HSW 604, 3rd and Parnassus Streets; San Francisco, Calif. 94143–0512). Anti $\beta_1$ integrin-function blocking antibodies are commercially available from mouse monoclonals from Chemicon International, JB1a or J10, catalogue #1965.

Example 1. Cell Proliferation Measurements

Cell proliferation was determined by 3 separate criteria: a) percentage of cells in S phase of the cell cycle (actively dividing) b) percentage of cells in the cell cycle and c) number of cells per spheroid.

When cultured within a 3 dimensional reconstituted basement membrane, non-malignant MECs undergo growth arrest after 6–10 days. In contrast MEC tumor cells fail to growth arrest and continue to grow. Restoration of non-malignant behavior by a treatment regime comprising application of $\beta_1$ integrin function-blocking antibody to tumor cells resulted in the ability of the tumor cells to growth arrest after 6–10 days when grown in a 3-D basement membrane. This was assessed by $^3$H thymidine labeling studies of day 10–12 cultures which determines the percentage of cells in S phase of the cell cycle. Three-dimensional cell cultures were pulse labeled with $^3$H thymidine for 24 hours after which the cultures were washed, fixed and frozen. Frozen sections were cut using a cryostat (5 micron sections) and overlaid with a film emulsion. The emulsion overlaid samples were exposed for one week after which they were developed with a standard Kodak developer and fixer. The total number of cells were counted and the number of $^3$H thymidine positive nuclei scored by the presence of silver grains over the cells. A minimum of 100–200 cells were scored per condition from separate experiments.

In FIG. 1, bar A shows the percentage of cells in S phase in 10–12 day cultures of non-malignant S-1 50 control cells, bar B shows tumor T-4 cells that have been "mock treated" by exposure to IgG$_1$, antibody to serve as a control for effect of non-specific antibody binding; and bar C shows $\beta_1$ integrin function-blocking antibody treated tumor T-4 cells. Non-malignant S-1 50 cells growth arrest after 8–10 days of culture within a 3 dimensional reconstituted basement membrane as indicated by a thymidine incorporation index of less than 5%. In contrast malignant T-4 cells failed to properly growth arrest within this timeframe and displayed a thymidine incorporation index of greater than 30%. Treatment of tumor cells with $\beta_1$ integrin function-blocking antibody resulted in a significantly decreased thymidine incorporation index, to less than 15%, suggesting the treatment was able to restore the growth inhibitory responsiveness of the tumor cells to the reconstituted basement membrane.

Cell proliferation was also assessed by scoring the percentage of Ki-67 positive cells. Ki-67 is a nuclear protein associated with proliferating cells and is absent in cells that have exited the cell cycle (that is, entered G$_0$). The presence of this protein was assessed by immunostaining frozen sections of 10-12 day 3 dimensional cultures with a monoclonal anti-human Ki-67 specific antibody, followed by detection with a Texas-red labeled anti-mouse secondary antibody and visualized by fluorescence microscopy. Positive cells indicate that the cell has remained within the cell cycle, i.e. G1-S-G2-M, while negative staining implies that the cells are probably in G$_0$ or no longer actively dividing. Indexes were determined by counting the number of Ki-67 positive nuclei and dividing this by the total cell count. A minimum of 200–400 cells were scored per condition from separate experiments. Non-malignant cells reach colony sizes of 6–8 cells after which they undergo growth arrest, exit the cell cycle, and commence morphogenesis.

In FIG. 2, the effect of treating cells with $\beta_1$ integrin function-blocking antibody is measured by immunostaining for the presence of nuclear Ki-67 proliferation associated protein in frozen sections of 3-dimensional, day 10–12, cultures of non-malignant S-1 50 control cells, A; mock treated tumor T-4 cells, B, and tumor T-4 cells treated with 1 integrin function-blocking antibody, C. Non-malignant S-1 50 cells exited the cell cycle after 8–10 days of culture within a 3 dimensional reconstituted basement membrane, as indicated by a Ki-67 labeling index of less than 10%. In contrast malignant T-4 cells treated only with non-specific IgG$_1$ antibody failed to exit the cell cycle within this timeframe and displayed a Ki-67 labeling index of greater than 35%, in a behavior typical of tumor cells. Treatment of tumor cells with $\beta_1$ integrin function-blocking antibody resulted in a significantly reduced Ki-67 labeling index, dropping to less than 20%. This suggests treatment with $\beta_1$ integrin function-blocking antibody restored the tumor cells' ability to exit the cell cycle when cultured in reconstituted basement membrane.

Data in FIG. 3 shows the ability of cells to respond to growth arrest cues, measured by counting the number of cells in each spheroid colony. The number of cells per colony and the final size of the colonies formed were measured. This was assessed by measuring the size of the 3 dimensional colonies of non-malignant, malignant and malignant cells restored to normal behavior in living basement membrane cultures. A minimum of 50–100 colonies were scored using a 10 X objective, phase contrast microscope fitted with an eye piece. The number of cells per colony was determined using frozen sections from 3 dimensional cultures, staining the nuclei using an intercalating DNA dye, DAPI, and counting the number of nuclei per colony.

In FIG. 3, Bar A shows the number of cells per spheroid in frozen sections of 3 dimensional, day 10–12, cultures of non-malignant S-1 50 control cells; bar B shows tumor T-4 cells treated with a mixture of non-specific rat IgG$_1$ antibody, and bar C shows tumor T-4 cells treated with $\beta_1$ integrin function-blocking antibody. Non-malignant S-1 50 cell spheroids contained between 6–8 cells per acini while typical T-4 cells, including those treated with a mixture of non-specific rat IgGs, formed colonies of between 20–30 cells. In contrast tumor cells treated with $\beta_1$ integrin function-blocking antibody formed colonies of between 6–8 cells, suggesting the treatment was able to restore the ability of the tumor cells to stop dividing at the appropriate spheroid cell number in response to cues from the reconstituted basement membrane.

Example 2. Morphology

Morphology was assessed using four criteria: a) colony organization; b) actin microfilament organization; c) formation of adherens junctions; and d) formation of $\beta_1$ catenin/E cadherin interactions.

FIG. 4 illustrates that non-malignant MECs undergo morphogenesis 8–10 days after culturing within a 3 dimensional basement membrane while tumor cells form large, disorganized colonies. Treatment with $\beta_1$ integrin function-blocking antibody allowed the tumor cells to form organized spheroids. The ability of cells to form organized colonies was assessed by examining colony structure in live 3 dimensional, day 10–12, cultures using a phase contrast microscope with a 10X objective. Organization was determined by measuring colony size, length and width, using an eyepiece objective with a ruler. Colonies were deemed organized if they were uniformly spherical and had well defined, rounded structures. At least 50–100 colonies were assessed per group in living basement membrane cultures. Bar A shows non-malignant S-1 50 cells; bar B shows tumor T-4 cells that were treated with a mixture of non-specific rat IgGs; and bar C shows tumor T-4 cells treated with $\beta_1$ integrin function-blocking antibody. Greater than 90% of non-malignant S-1 50 cells grew as organized, spherical acini, while the majority of the rat IgG-treated tumor cells formed large, disorganized colonies. In contrast 75% of the colonies formed by tumor cells treated with $\beta_1$ integrin function-blocking antibody grew as spherical, well organized, acini. This indicates that the $\beta_1$ integrin function-blocking antibody treatment was able to promote the formation of organized structures by the tumor cells.

Figure 5:
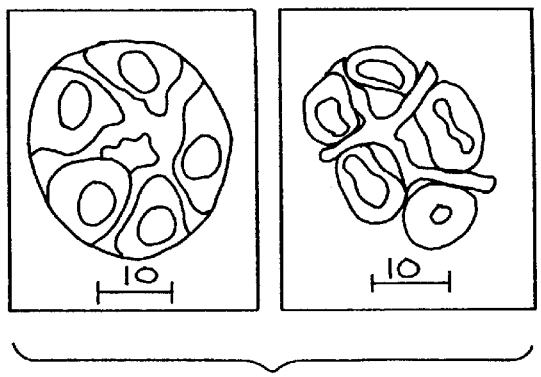
Figure 5:
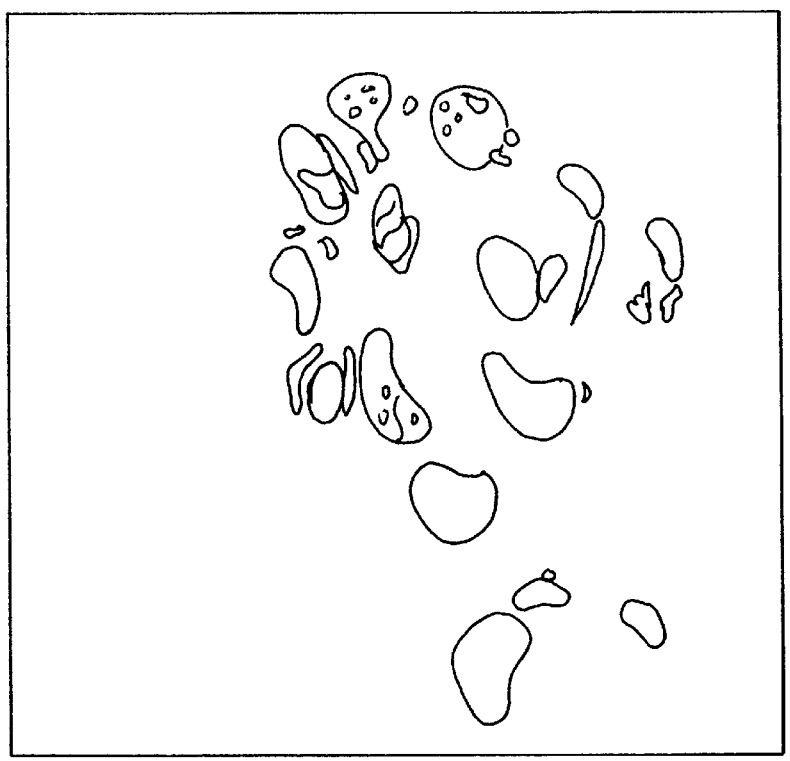
Figure 5:
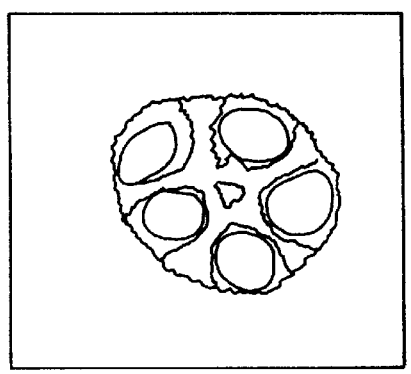

FIG. 5 provides a schematic representation of the presence of organized filamentous actin, which reflects the cells' ability to organize their cytoskeletons. The filamentous actin was visualized using FITC-labeled phalloidin (FITC is a fluorescent dye), and a fluorescence microscope. Colonies were scored according to their degree of organization based on the behavior of the actin staining in 3 dimensional stained colonies of non-malignant MECs. A minimum of 50–100 colonies were scored. All colonies formed by both the non-malignant S-1 50 and tumor cells treated with $\beta_1$ integrin function-blocking antibodies were found to have organized actin filaments.

Frame A shows filamentous actin typical of that found in frozen sections of 3 dimensional cultures of day 10–12 non-malignant S-1 50 MEC cells; frame B shows results typical of rat IgG control-treated tumor T-4 cells; and frame C shows results typical of tumor T-4 cells treated with $\beta_1$ integrin function-blocking antibody. Non-malignant S-1 50 colonies exhibited well organized filamentous actin lateral staining which reflected the spherical structure of the acini. In contrast T-4 tumor cells demonstrated punctate, disorganized sparse actin staining with visible crystalline deposits of actin bundles. Treatment of tumor cells with the $\beta_1$ integrin function-blocking antibody restored the actin staining towards that observed in the non-malignant S-1 50 cell acini.

In FIG. 6, the cells ability to form adherens junctions was measured by staining E cadherin, a well characterized adherens junction protein, so it could be visualized using fluorescence microscopy. Cellular E cadherin was stained by incubating the cells with a rat anti-human E cadherin monoclonal antibody, and visualizing this anti-rat Texas red labeled secondary antibody with fluorescence microscopy. The appearance of cell—cell staining and lack of cytosolic staining indicated the presence of adherens junctions. The results obtained in tumor T4 cells showed that most of the E-cadherin protein was dispersed throughout the cytoplasm and not localized to cell—cell interaction areas consistent with loss of cadherens junction assembly. Colonies were scored as positive for cell—cell adherens junction staining or negative when they showed high cytosolic or lack of cell—cell staining. A minimum of 100 different cell colonies were scored from different experiments. All non-malignant cells were found to have uniform cell—cell E cadherin junction staining while none of the tumor cells did.

Frame A shows results of typical adherens junction staining patterns assessed by immunostaining of frozen sections of day 10–12 non-malignant S-1 50 cells; frame B shows typical adherens junction staining pattern for control, non-specific rat IgG antibody-treated, tumor T-4 cells; and frame C shows typical adherens junction staining pattern for tumor T-4 cells treated with $\beta_1$ integrin function-blocking antibody. Non-malignant S-1 50 cell colonies had visible adherens junctions as evidenced by intense cell—cell lateral staining of E cadherin. In contrast, the control, rat IgG antibody-treated, tumor cells demonstratedhigh cytosolic E cadherin staining and only random, punctate cell—cell staining. Tumor cells treated with $\beta_1$ integrin function-blocking antibody formed cell-cell lateral E cadherin staining, although basal staining was also evident. These cells also had no evidence of cytosolic E-cadherin staining.

In FIG. 7, the cells' ability to form beta-catenin/E-cadherin interactions was determined by immunoprecipitating total E-cadherin protein from equal numbers of cells, using a mouse anti-human E-cadherin monoclonal antibody. The immuno-precipitate was run on sodium diodecyl sulfate polyacrylimide gel electrophoresis (SDS PAGE) reducing gels and transferred to nitrocellulose membranes (blots). The blots were then probed for the presence of E cadherin or beta-catenin using human specific anti-E cadherin or anti-beta-catenin antibodies which were then detected by anti-mouse horse radish peroxidase secondaries and enhanced chemiluminescense (ECL). Amount of immuno-precipitable E-cadherin and the beta catenin associated with the E cadherin was assessed by densitometric scanning of the western blots. Data was expressed as a percentage of beta catenin precipitated down with the E cadherin and compared to that immunoprecipitated down with the E cadherin protein in non-malignant MEC cultures. Data is the average of at least 3 experiments.

The existence of beta-catenin/E cadherin interactions, which has been shown to be critical for the formation of adherens junctions, was assessed in day 10–12, 3-dimensional cultures of S-1 50 non-malignant cells, bar A; control rat IgG-treated tumor T-4 cells, bar B; and tumor T-4 cells treated with $\beta_1$ integrin function-blocking antibody, bar C. This was assessed by immunoprecipitating equal cell numbers of 3 dimensional cultures of each of the groups with an anti-human E cadherin antibody, followed by quantification of total E cadherin and co-precipitated beta-catenin by immunoblotting and densitometric analysis. The non-malignant S-1 50 cells immunoprecipitated equal quantities of beta-catenin and E cadherin while the control rat IgG-treated tumor cells co-precipitated only 30% of the quantity of beta-catenin observed in the non-malignant cells. Treatment of tumor cells with the $\beta_1$ integrin function-blocking antibody increased the beta-catenin co-precipitated with the E cadherin up to 75% of that associated with the non-malignant S-1 50 cell E cadherin. These results suggest that the treatment tumor cells with $\beta_1$ integrin function-blocking antibody was able to restore the ability of beta-catenin to interact with E cadherin and thereby facilitate the formation of adherens junctions.

Example 3. Responsiveness to a basement membrane

The ability cells to respond to the presence of an exogenous basement membrane was assessed by two criteria: a)

the cells' ability to organize their own endogenous basement membranes and b) the cells' ability to repress apoptosis. Non-malignant MECs respond to an exogenous basement membrane by synthesizing and organizing an endogenous basement membrane around their acini and repressing apoptosis.

FIG. 8: The presence of an endogenous basement membrane was assessed by immunostaining frozen sections of day 10–12, 3-dimensional cultures for the presence of basally deposited collagen IV, using an anti-human collagen IV antibody (a known constituent of the endogenous basement membrane).

In FIG. 8, frame A shows the endogenous basement membrane indicated by collagen type IV or laminin of non-malignant S-1 50 control cells; frame B shows a schematic representation of endogenous basement membrane surrounding mock rat IgG antibody-treated tumor T-4 cells; frame C shows the endogenous basement membrane surrounding tumor T-4 cells that were treated with $\beta_1$ integrin function-blocking antibody. Non-malignant S-1 50 cells undergo growth arrest, form organized acini and deposit an organized basement membrane in response to a reconstituted exogenous basement membrane. In contrast tumor cells that are untreated with antibody or are treated with a mixture of nonspecific rat IgGs, fail to undergo growth arrest; instead they form unorganized, large colonies and do not deposit a basal endogenous basement membrane. Treatment of tumor cells with $\beta_1$ integrin function-blocking antibody leads to the deposition of an organized basement membrane suggesting the tumor cells were now responding appropriately to cues from the exogenous basement membrane.

FIG. 9: The ability of cells to repress apoptosis was assessed in frozen sections of 10–12 day, 3-dimensional cultures by checking for the presence of DNA nicks using terminal transferase FITC dUTP end-labeling (TUNEL labeling) of apoptosis specific endonuclease mediated DNA breaks. This was followed by visualization using fluorescence microscopy. Apoptosis rates were scored as the number of positively labeled nuclei per total cell count. A minimum of 100–200 cells were scored from different experiments.

In bar A FIG. 9 shows the TUNEL labeling index of day 10–12, 3-dimensional cultures of non-malignant S-1 50 control cells; bar B shows the TUNEL labeling index of control non-specific rat IgG-treated T-4 tumor cells; and bar C shows T-4 tumor cells treated with $\beta_1$ integrin function-blocking antibody. Non-malignant MEC cells respond to an exogenous basement membrane by inhibiting basal apoptosis as evidenced by an apoptotic index of less than 2%. In contrast tumor cells treated with nonspecific Ab do not respond appropriately to cues from the ECM and exhibit elevated basal apoptosis rates of greater than 20–30%. Treatment of tumor cells with $\beta_1$ integrin function-blocking antibody resulted in a significant reduction in basal apoptosis rates of less than 15% suggesting the treatment permitted the tumor cells to respond appropriately to the exogenous basement membrane microenvironment.

Example 4. In vivo tumorigenicity

The ability to repress tumorigenicity in vivo was assessed by injecting tumor cells subcutaneously into nude mice. Before injection, the cells were embedded in EHS matrix for about three or four days. The cells were released by dispase treatment and subjected to one of three regimens for 3–4 hours depending on whether they were controls, treated, or untreated cells, as follows: -controls, medium containing non-specific rat IgGs; -treated cells, medium containing rat monoclonal anti human $\beta_1$ integrin function-blocking antibody; or -untreated cells, standard medium not containing antibody. Non-malignant MECs do not form tumors in vivo when injected subcutaneously into nude mice, even after 2–3 months.

Untreated T-4 tumor cells, T-4 tumor cells treated with nonspecific IgG antibodies, and T-4 tumor cells treated with $\beta_1$ integrin function-blocking antibody, were injected subcutaneously into different groups of nude mice. In all cases, between about $1 \times 10^6$ and about $4 \times 10^6$ tumor cells were injected and the mice were monitored for the formation of tumors. After one to two months the mice were sacrificed and the presence and size of tumors were analyzed. If tumors were found they were excised and measured. The results are tabulated in Table II, below.

TABLE II

In Vivo Turmorigenicity

| Treatment Groups | Mice having Large Tumors[1] | Mice having Small Tumors[2] | Mice having No Tumors |
|---|---|---|---|
| T-4 tumor cells untreated before injection | 14/16 | 1/16 | 1/16 |
| T-4 tumor cells treated with nonspecific IgGs before injection | 11/16 | 3/16 | 2/16 |
| T-4 tumor cells treated with $\beta_1$ integrin function-blocking antibody before injection | 5/16 | 2/16 | 9/16 |

[1]tumors between about 5 mm$^3$ and about 300 mm$^3$
[2]tumors less than about 5 mm$^3$ Two experiments were performed resulting in a total of 16 mice per treatment group being assessed. Table II summarizes the results. Untreated T-4 tumor cells formed tumors in nude mice 95% of the time. Fewer than 50% of the nude mice injected with T-4 tumor cells that had been treated with $\beta_1$ integrin function-blocking antibody before injection produced tumors. In addition the average tumor volume was significantly smaller in the group of mice that received cells treated with $\beta_1$ integrin function-blocking antibody than in the group of mice that had received cells that had not been so treated.

Example 5. Inducement of normal colony morphogenisis by antibody or Ab fragment (FAB) binding to $\beta_1$ integrin-function receptor.

T4–2 tumor cells were propagated as monolayers until confluent. They were then trypsinized and seeded into a 3D cell culture matrix as described above.

Different goups of 3D cultures were incubated in the presence of comparable, incremental protein concentrations of integrin antibodies or control nonspecific IgGs. Between about 25 µg antibody protein/ml matrix solution and about 200 µg antibody protein/ml matrix solution was used. Using four different antibodies (a control and three anti-$\beta_1$ integrin monoclonal antibodies or fragments thereof) four groups of 3D cultures were assessed for the affect of the antibodies on cell colony morphorgenisis and therefore on colony growth. The antibodies used were, 1) nonspecific IgG control antibodies; 2) anti-$\beta_1$ integrin mAb AIIB2, obtained from C. Damsky; 3)anti-$\beta_1$ integrin mAb JB1a (also designated J10), obtained from Chemicon International; and 4) anti-$\beta_1$ integrin mAb TS2/16, obtained from Dr. Martin E. Hemler (Department of Pathology, Dana-Farber Cancer Institute, Harvard University, 44 Binney Street, Room M-613, Boston, Mass. 02115–6084).

After 12 days incubation in 3D culture matrix, the diameters of between 100 and 400 colonies were measured for each antibody-treated group and for parallel cultures of S-1 nonmalignant cells. The mean diameters of malignant cell colonies were divided by the mean diameters of nonmalignant cell colonies and expressed as a percent, ±standard error. The results are shown in Table III.

TABLE III $\beta_1$ Integrin Antibody Treatment And T4-2 Tumor Colony Morphology After 12 Days Of Culture In 3D Culture Matrix

| ANTIBODY TREATMENT | MEAN MALIGNANT COLONY DIAMETER EXPRESSED AS A PERCENT OF MEAN NON-MALIGNANT COLONY DIAMETER ± SEM | AFFECT OF ANTIBODY TREATMENT ON COLONY GROWTH |
|---|---|---|
| control, non-specific IgGs | 303.2 ± 2.7 | |
| AIIB2, crude Ascites, dialyzed | 98.2 ± 9.9 | inhibited |
| AIIB2 purified IgG$_1$ dialyzed | 115.1 ± 4.4 | inhibited |
| AIIB2 Fab fragments, dialyzed | 103.6 ± 4.1 | inhibited |
| J10, crude Ascites, dialyzed | 131.8 ± 5.9 | inhibited |
| TS2/16, crude Ascites, dialyzed | 251.9 ± 13.4 | |

When treated with control antibodies, tumor cells grew into colonies that had diameters approximately 300 times larger than normal cell colonies. In contrast, when malignant cells were treated with AIIB2 or J10 antibodies, cell colony morphogenisis was induced and thus colony growth was inhibited. Interestingly, malignant cells treated with TS2/16 antibodies grew to size almost equal to the controls.

Significantly, both purified AIIB2 mAb and its mAb Fab fragments were capable of inducing the phenotypic reversion of the T4–2 tumor cells at similar protein concentrations.

Example 6. Cancer therapy

A biopsy of tumor or tumor tissue fragments are treated with proteolytic enzymes and separated into component parts as described by Petersen et al. (PNAS 92; Breast J. 1995). They are grown in 3-D culture matrix and integrin and cell adheren molecules characteristics are assayed as described above.

Based on the behavior of the biopsy cells in these conditions, the clinician can predict the type and nature of treatment a patient should receive. Furthermore, after treatment is in progress, the inventive assay will provide a critical tool to determine the degree to which patient treatment has resulted in changing the profile of surviving cells. This would trigger the clinician to modify the treatment program accordingly.

Possible Mode of Action of the Invention

Experiments suggest some possible mechanisms by which the $\beta_1$ integrin function-blocking antibodies reverse the malignant phenotype. Discussion of these mechanisms serve as an example by which the invention works and are not intended to limit the scope of the invention to those mechanisms.

It has been shown that application of $\beta_1$ integrin function-blocking antibodies to normal cultured breast epithelial cells in a 3-D reconstituted basement membrane can cause the cells to die before they have formed an organotypic structure. This is because normal non-malignant MEC's rely on signals from the basement membrane transduced via their $\beta_1$ integrin receptors for survival. Binding integrin function-blocking antibodies to surface $\beta_1$-integrins of non-malignant cells prevents competent cell-ECM interaction from occurring and the cells die. In contrast, cells that already express the malignant phenotype (because of, for example, genetic mutations that effect the expression, localization, or downstream signaling events of their integrin receptors) respond to such binding events differently than normal cells. Application of $\beta_1$ integrin antibodies to malignant cells may reduce excessive receptor levels at the cell surface and allow the cells to express contact inhibition of growth and proper structure and signaling capability, thus greatly reducing the threat of the malignant growth. Alternately, this may repress signaling from one group of integrin receptors and allow for higher signal inputs from another group. Finally the antibody might induce conformational changes in the cell surface integrin receptors thereby permitting proper signal transduction to occur.

In a nonmalignant cell, the $\beta_1$ integrin resides within the cell membrane having one end extending into the cell cytoplasm (the cytoplasmic tail) and the other end (the receptor, comprising the extracellular N terminus) residing on the outside surface of the membrane. The cytoplasmic tail of the $\beta_1$ integrin associates with complex actin networks that in turn are thought to mediate signaling to the cell nucleus. Adhesion of $\beta_1$ integrins with their ECM substrates appears to induce clustering in normal cells, which may stabilize the connection between the intercellular structure and the extracellular receptors, allowing signals arising from the ECM-receptors to transmit toward the interior of the cell. Conformation induced signaling may require auxiliary factors for full effects. This auxiliary factor may be missing in tumor cells and the antibody may be replacing that factor's function. High antibody concentrations would be expected to impede that auxiliary protein function in non-malignant cells thereby preventing signaling and killing the cells.

In contrast, in a malignant cell, the $\beta_1$ integrins do not cluster, and preformed glycosylated non-dimerized integrin is frequently found in the cytoplasm of the cell, disconnected from the cytoskeleton. The inventors postulate that the $\beta_1$ integrin Ab may a) promote $\beta_1$ integrin receptor cell surface expression or induce an inactive conformational change in the receptor ligand binding domain, or b) promote clustering through conformational changes, cross-linking, or stabilizing (thereby forcing clustering) thus reintroducing a structural integrity to the molecular tranduction apparatus. In effect, the $\beta_1$ integrin antibody may titrate down the abnormal receptor level on the exterior surface of the cell, restore proper balance, and force clustering.

Thus, the invention provides a means to reverse malignant expression in carcinomas and limit or prevent their metastasis by applying $\beta_1$ integrin Ab, or peptides related to the Ab binding site, to the exterior of the cells.

The description of illustrative embodiments and best modes of the present invention is not intended to limit the scope of the invention. Various modifications, alternative constructions and equivalents may be employed without departing from the true spirit and scope of the appended claims.

Having thus described the invention, what is claimed is:

1. A method to reverse expression of malignant phenotypes chosen from the group consisting of growth control, apoptosis control, cell colony organization, actin organization, formation of adherens junctions, and responsiveness to presence of basement membrane in cultured mammalian breast cells comprising, applying $\beta_1$ integrin specific antibody or a $\beta_1$ integrin specific binding fragment thereof or a $\beta_1$ integrin specific binding peptide therefrom to the cells.

2. The method of claim 1 wherein the $\beta_1$ integrin specific antibody or a $\beta_1$ integrin specific binding fragment thereof or a $\beta_1$ integrin specific binding peptide therefrom is applied in the presence of a three dimensional culture matrix.

3. The method of claim 1 wherein the concentration of $\beta_1$ integrin specific antibody is 50 $\mu$gram/ml to 1000 $\mu$gram/ml IgG$_1$ in a biologically compatible solution.

4. The method of claim 1 wherein the concentration of $\beta_1$ integrin specific antibody is 500 $\mu$gram/ml to 10 $\mu$gram/ml IgG$_1$ in a biologically compatible fluid.

5. The method of claim 1 wherein the concentration of $\beta_1$ integrin specific antibody is 100 $\mu$gram/ml IgG$_1$ in a biologically compatible fluid.

6. The method of claim 1 wherein the concentration of $\beta_1$ integrin specific antibody is 1 mg/ml IgG$_1$ in a biologically compatible fluid.

7. The method of claim 1 wherein the antibody is chosen from the group consisting of antibodies to $\beta_1$ integrin, rat monoclonal AIIB2, mouse monoclonal JB1a also referred to as J10 (chemicon catalogue#1965, and peptides that bind to the functional integrin site, suspended or dissolved in an appropriate solution.

8. A method for reversing expression of malignancy in mammalian cells according to claim 1 further comprising the steps of, a) mixing a three dimensional culture matrix compound with $\beta_1$ integrin specific antibody or a $\beta_1$ integrin specific binding fragment thereof or a $\beta_1$ integrin specific binding peptide therefrom;

b) placing the mixed three dimensional culture matrix on the bottom of a culture dish;

c) incubating dishes containing matrix at about 37° C. until matrix hardens;

d) obtaining an approximately single cell suspension of malignant phenotype cells to be treated;

e) gently microfuging the cells out of solution;

f) gently resuspending the cells in about 300 $\mu$l mixed three-dimensional culture matrix and $\beta_1$ integrin function-blocking reagent;

g) transferring the cells to culture dishes containing hardened matrix;

h) incubating the transferred cells at about 37° C. for about one hour; and i) adding between about 500 $\mu$l and about 2,000 $\mu$l of serum free medium with additives and replacing cultures in an incubator.

* * * * *